United States Patent
Hung et al.

(10) Patent No.: US 8,054,950 B1
(45) Date of Patent: Nov. 8, 2011

(54) NETWORK INITIATION AND PULL OF MEDIA FROM MOBILE DEVICES

(75) Inventors: Yat-Sang Hung, San Diego, CA (US); Pierre Barbeau, Leawood, KS (US)

(73) Assignee: Sprint Spectrum L.P., Overland Park, KS (US)

( * ) Notice: Subject to any disclaimer, the term of this patent is extended or adjusted under 35 U.S.C. 154(b) by 1506 days.

(21) Appl. No.: 11/155,705

(22) Filed: Jun. 17, 2005

(51) Int. Cl.
*H04M 1/64* (2006.01)
*H04M 11/00* (2006.01)
*G06F 15/167* (2006.01)
*G06F 15/16* (2006.01)
*G06Q 10/00* (2006.01)

(52) U.S. Cl. ........... 379/88.17; 379/88.13; 379/88.14; 379/88.18; 709/214; 709/227; 725/24; 705/2

(58) Field of Classification Search .......... 370/388, 370/390, 352; 379/88.13, 265.01; 705/26, 705/432
See application file for complete search history.

(56) References Cited

U.S. PATENT DOCUMENTS

| | | | | |
|---|---|---|---|---|
| 5,970,122 A | * | 10/1999 | LaPorta et al. | 340/7.23 |
| 6,314,285 B1 | * | 11/2001 | Isberg et al. | 455/418 |
| 7,099,659 B1 | * | 8/2006 | Schnake et al. | 455/419 |
| 7,366,285 B2 | * | 4/2008 | Parolkar et al. | 379/88.17 |
| 2002/0055861 A1 | * | 5/2002 | King et al. | 705/4 |
| 2002/0137528 A1 | | 9/2002 | Fraccaroli | 455/457 |
| 2002/0147661 A1 | * | 10/2002 | Hatakama et al. | 705/26 |
| 2004/0203946 A1 | * | 10/2004 | Wu et al. | 455/466 |
| 2005/0266831 A1 | * | 12/2005 | Roth | 455/412.1 |
| 2006/0066448 A1 | * | 3/2006 | Berisford et al. | 340/504 |

OTHER PUBLICATIONS

WAP™ MMS Architecture Overview, Version Apr. 25, 2001 ©2001, Wireless Application Protocol Forum, Ltd.
"Sending MMS Notifications and Content" (date and author unknown).

* cited by examiner

*Primary Examiner* — MD S Elahee
*Assistant Examiner* — Solomon Bezuayehu

(57) ABSTRACT

A messaging service node sends encoded messages to wireless devices prompting the devices to capture media (e.g., audio and/or image) and send the media file to a network address specified in the message. The service node may be managed by a wireless service provider, and provides this media capture message service for unrelated, independent entities such as insurance companies, health or medial companies, government agencies, etc. The encoded message may take the form of a Multimedia Messaging Service (MMS) message, but other formats are possible. The media is preferably captured by a camera or microphone incorporated into the wireless device.

20 Claims, 4 Drawing Sheets

NETWORK INITIATION AND PULL OF MEDIA FROM MOBILE DEVICES

BACKGROUND

A. Field

This invention relates generally to communications between wireless communications devices (cell phones, personal digital assistants, laptop computers with wireless modems, and the like) and network entities on a packet switched network. More particularly, it relates to a method for automatically prompting a wireless device to capture media (preferably with a media capture mechanism included with the device) and send the media over a radio access network to a receiving network node on a packet switched network.

B. Related Art

It is generally known today for wireless communication devices (WCDs), such as cell phones and wirelessly equipped computing devices such as personal digital assistants (PDAs) and laptop computers to be able to engage in wireless packet-data communications and to thereby wirelessly send and receive messages and other content from land-based network entities. A wireless service provider, for instance, may provide a radio access network (RAN) and packet-data serving node (PDSN) that cooperatively establish wireless packet-data connectivity between a WCD and a packet-switched network such as the Internet or a private packet network.

In usual practice, a WCD initiates acquisition of a packet-data connection by sending a packet-data origination message over an air interface access channel to the carrier's RAN. In response, the RAN then assigns an air-interface traffic channel for use by the WCD, and the RAN signals to a packet data serving node (PDSN) or other gateway, which negotiates with the WCD to set up a data link layer connection. In addition, the gateway or a mobile-IP home agent assigns an IP address for use by the WCD to engage in packet-data communications. The WCD may then communicate with other entities on the packet-switched network in much the same way as a traditional personal computer would, except that the WCD would communicate over a wireless air interface and via the RAN.

One difficulty with this kind of arrangement is that, depending on configuration, it typically precludes pushing of packet-data communications to a WCD, i.e., sending of packet-data to a WCD without the WCD initially requesting the data. Rather, in order for a WCD to receive packet-data, the WCD must usually first acquire packet-data connectivity and then request the data. For instance, to receive content from a particular URL, the WCD must first acquire packet-data connectivity and then send an HTTP request seeking content from that URL.

One well-accepted way to overcome this limitation is to send a specially-coded data-notification message over an air interface control channel to the WCD, such that the WCD receives the data-notification message without needing to acquire packet-data connectivity. The data-notification message may take the form of an SMS message of the type defined by industry standard protocol published as EIA/TIA IS-637 for instance, carrying a special code that designates it as a data notification message and carrying a URL of a network location where the data to be delivered is stored. Upon receipt of such a data-notification message (and detection that it is such a message), the WCD may then automatically acquire data connectivity and send an HTTP request to obtain the data from the designated URL.

Systems that deliver data in this manner go by various names, such as "WAP Push" and, more recently, "Multimedia Messaging Service" (MMS) (which actually uses WAP Push technology). These techniques are known in the art and described in the relevant standards documents and associated technical literature, therefor a detailed description is omitted for the sake of brevity. MMS messaging, for instance, is commonly used to send media such as digital images or video clips to a WCD. MMS architecture is described generally in the document WAP MMS Architecture Overview, Version 25 Apr. 2001, published by the Wireless Application Protocol Forum, Ltd., the contents of which are incorporated by reference herein.

To send an MMS message to a WCD, for instance, a server or other message-sender delivers to an MMS server an MMS message file that contains an MMS header followed by a multipart binary MIME message defining the content. The server then stores the MMS message and transmits a subset of the MMS header as an MMS notification message (MMS message type "m-notification-ind") via SMS to the WCD together with a URL pointer to a location of the complete message on the MMS server. Upon receipt of the MMS notification message, program logic on the WCD would then automatically send an HTTP request to download the message from the designated URL.

Thus, it is known for the WCD station to present a pop-up message to a user and, typically after user consent, to then go to the designated URL (i.e., send an HTTP message to the URL) to get the content. That process facilitates "pushing" content to the mobile station.

The present invention provides methods by which a WCD may be automatically prompted to transmit media content (e.g., audio recording such as voice, or photographs or video imagery) to a network node. In contrast to the above-described content "push" methods, the present invention may be considered a sort of "pull" method since it "pulls" content from the device instead.

Fraccaroli, U.S. Patent Application Publication 2002/0137528 dated Sep. 26, 2002, describes a method by which digital images created by a mobile station are provided to an assistance center, such as a "911" type emergency dispatch center. The image is created automatically upon initiation of a request for assistance from the assistance center at the mobile station. While the '528 patent application discloses a method of sending media from a wireless device to an assistance center, it does not contemplate or suggest a network entity automatically providing prompts or other input to stimulate generation of media content and transmitting the content from the mobile station to a network node, and thus does suggest features of this invention. Nor does it contemplate a system in which a messaging service node managed by a wireless service provider provides media capture messaging services for unrelated entities, e.g., insurance companies or health care companies.

SUMMARY

In a first aspect, a method is provided for obtaining media from a wireless communications device. The term "wireless communications device" is intended to be interpreted broadly to encompass cellular telephones, personal digital assistants, or other portable communications devices that are capable of communication with a network entity on a packet switched network via a radio access network, e.g., CDMA cellular telephone network.

The method comprises a step of sending an encoded message from a message service node to the wireless device. The encoded message, which may take the form of a scheduling message, includes a prompt displayable at the wireless device prompting or reminding the user of the wireless device to capture media. The message includes a scheduling feature (e.g., date or time, or other information) that indicates when the prompt is to be displayed. The message further includes a network address (e.g., in the form of a URL link) where the captured media is to be sent by the wireless communications device.

Thus, the wireless device receives the message and then a prompt in accordance with the message is displayed. The prompt is displayed at a time according to the schedule feature. The time may be immediate upon receipt of the message, later at a designated time, or periodically, e.g., every day at a certain time. The media is then captured (preferably by a camera or microphone built into the device, but this is not necessary), and the media is sent to the address specified in the message.

In one typical embodiment, the media comprises an image and the message prompts the wireless device to capture the image with a camera incorporated into the device. In another typical embodiment, the media may consist of audio, such as the voice, musical recording, or other sound.

The message format for the encoded message may take a variety of formats. One presently preferred format is that of a Multimedia Messaging Service (MMS) message.

The situation may arise that the device is turned off, is busy when the message is sent, or the message fails to be delivered to the device. Accordingly, in another aspect, the message service node preferably includes a queue or buffer for storing the message, and the message is sent at a later time. In another aspect, a prompt message is sent periodically to the wireless device, e.g. once a day or once a week.

The invention can be implemented as a system including a message service node which provides messaging services for a plurality of wireless communications devices. In this situation, the message service node is preferably managed by a provider of wireless communications services and provides messaging services for a number of subscribers to the service provider. The prompt message can be generated by a network node different from the message service node and transmitted to the message service node for transmission to the wireless communications devices. For example, the network node generating the messages could be a network node managed by a unrelated entity such as an insurance company, health or medical company, government agency, entertainment company, repair shop, or other type of entity. The message service node provides a clearinghouse which collects all these messages, formats them if necessary in accordance with the required format for the message (e.g., in MMS form) and then sends them to the wireless devices on behalf of the entities that generated the prompt messages.

In another aspect of this invention, a wireless communications device is provided that facilitates media "pull" from a network node. The device comprises transmit and receive circuitry for communications with the network node over a radio access network; a graphical user interface presenting prompts and information to the user of the device; and a processor executing software instructions loaded in memory on the device. The software instructions include instructions for the processor to process an encoded message from a message service node and responsively display a prompt on the graphical user interface associated with the message. The prompt prompts the user of the device to transmit a media file to the network node. The prompt message includes a network address where the media file is to be transmitted, and this address may be displayed in the form of a hyperlink.

DETAILED DESCRIPTION OF PREFERRED EMBODIMENT

Before describing a representative system and method for practicing the invention, a brief overview and example will be provided. Consider a hypothetical situation where a user needs to do something at a specific time, and media capture is associated with the activity. For instance, the user may have signed up for a weight loss program, or may have been released from the hospital under circumstances where the user is required to take pictures of their meals and send those pictures to a network node, e.g., central server of a weight loss clinic or medical facility. This invention provides a mechanism by which the pictures are uploaded to the network node.

The system includes a message service center or node that sends a coded message to the wireless device associated with the user. The message includes a prompt feature, a scheduling feature, and a network address. The prompt feature causes a pop-up or prompt to appear of the graphical user interface of the device that prompts the user to capture media. The prompt appears at a time dictated by the scheduling feature. The prompt includes a network address (e.g., hyperlink) of where to send the picture. Once the user takes a picture, they use the user interface features to send the picture to a designated server.

The coded message may take the form of a scheduling message (e.g., a specially coded SMS message) that is sent to the wireless communications device. The device include a processor executing software instructions, including software instructions in the form of logic to process the encoded message to display the prompt to capture media (photo, video, audio, etc.). The prompt is displayed at the time dictated by the scheduling feature in the encoded message.

The media to be captured will typically consist of audio and/or images (still or video). The media capture preferably takes place via a camera or microphone that is built into the wireless communications device, therefore eliminating the need for a separate device to capture the media and transmit the media to the wireless device.

A. System Overview

Figure 1:
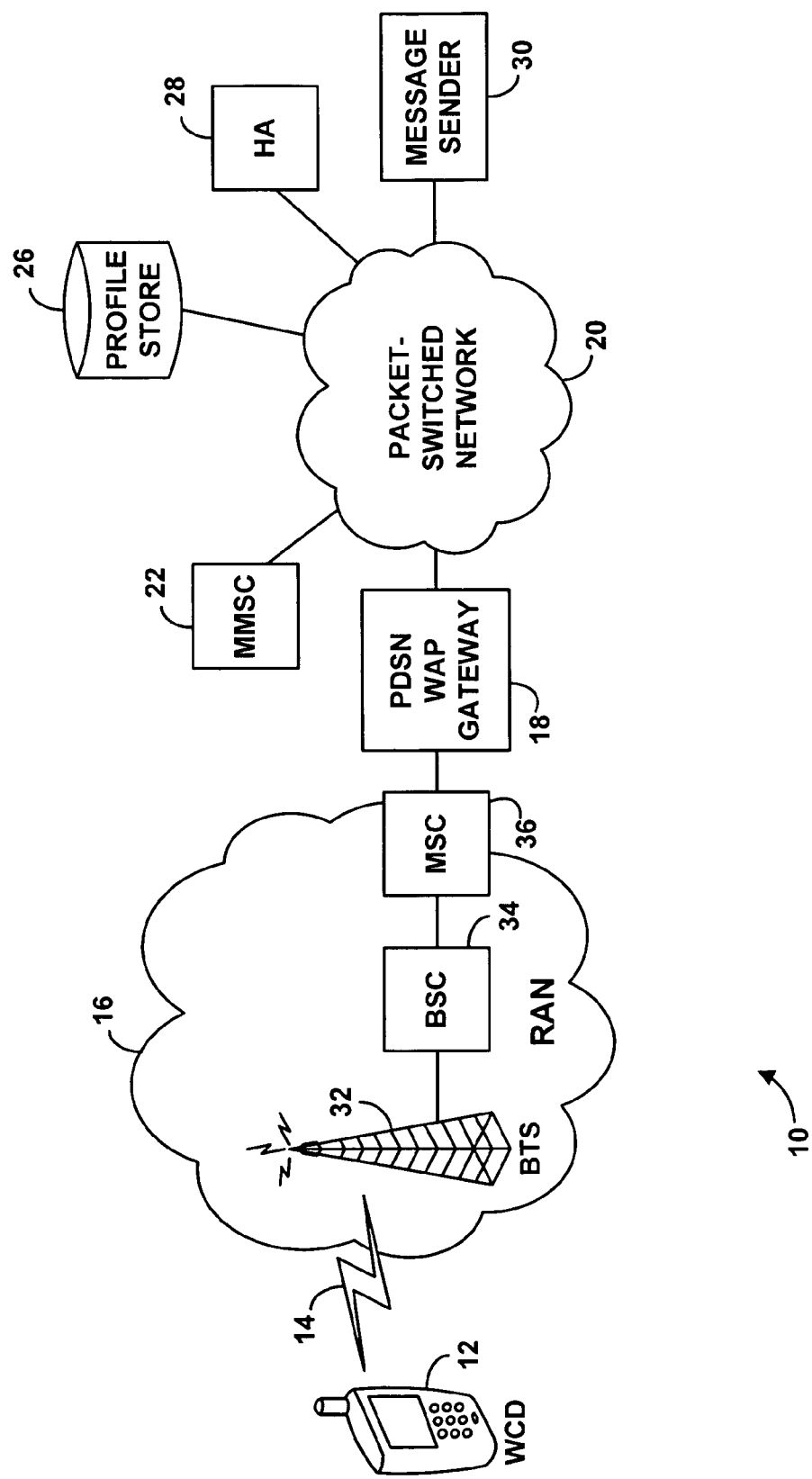
FIG. 1 is a network diagram of a environment in which the invention can be practiced, showing the wireless communications device, messages service center node (MMSC) and a network node "message sender" that originates the prompt message for transmission to the wireless device.

Referring to the drawings, FIG. 1 depicts an exemplary network 10 in which an embodiment of the present invention can be implemented. Of course, this and other arrangements and processes depicted and described herein are set forth for purposes of example only and that many variations are possible. For instance, structural elements and/or process steps can be added, omitted, combined, distributed, or re-arranged.

Further, it should be understood that the various functions described herein can be carried out by one or more elements equipped with any combination of hardware, firmware, and/or software, such as a microprocessor programmed with machine language instructions for carrying out the functions.

Exemplary network 10 includes a wireless communication device (WCD) 12 coupled by an air interface 14 with a radio access network (RAN) 16, and a packet-data serving node (PDSN) 18 providing a connection between the RAN 16 and a packet-switched network 20. Sitting as nodes on the packet-switched network 20 or otherwise accessible via the packet-switched network are then an MMS service center (MMSC) 22 which functions to send MMS messages to the wireless device 12, a gateway 24, a subscriber profile store 26, a mobile-IP home agent 28, and a network node 30 that is a message generator and sender. The MMSC 22 may be managed by a wireless service provider providing voice and data services for wireless subscribers, including device 12. The node 30 may be independently managed, e.g., by a commercial or governmental entity that is unaffiliated with the wireless service provider. The MMSC 22 forwards prompt messages to the device 12 on behalf of the network node 30.

The prompt messages generated by node 30 will typically include the scheduling feature (date, time and/or periodic basis on which to display the prompt) since the node 30 is the entity that is most concerned with the display of prompt messages and media capture and presumably knows when it wants such messages displayed on the wireless device. For example, if the node 30 is a health care facility, it knows that a given patient was released from the hospital on a certain day and may wish to have the patient provide photos of the meals eaten by the patient (or other information such as medications taken, or other photos) and will know when it wants to have such photos taken and on what periodic basis.

WCD 12 may be any sort of wireless communication device. By way of example, WCD 12 may be a cellular telephone, a wirelessly equipped personal digital assistant, a wirelessly-equipped personal computer, a wirelessly-equipped camera, or other sort of device that is able to receive data-notification messages and engage in wireless packet-data communications.

RAN 16 can take various forms. By way of example, RAN 16 is shown to include a base transceiver station (BTS) 32, a base station controller (BSC) 34, and a mobile switching center (MSC) 36. BTS 32 includes one or more antenna elements communicate over air interface 14 with WCD 12. BSC 34 then controls BTS 32 and generally governs communications over air interface 14, such as the allocation of frequencies, traffic channels, and the like. MSC 36, in turn, generally controls RAN 16 and may provide connectivity with the public switched telephone network (not shown). Further, MSC 36 is coupled by a signaling path 38 with MMSC 22, to facilitate delivery of MMS notification messages to WCDs such as WCD 12. As example variations on the RAN arrangement shown, the functions of BTS 32 and BSC 34 can be integrated together, and the functions of BSC 34 and MSC 36 may be integrated together.

RAN 16 and WCD 12 preferably communicate with each other according to an agreed air interface protocol, such as CDMA, TDMA, GSM, 802.11, or some other protocol now known or later developed. In a preferred embodiment, the air interface protocol is CDMA.

PDSN 18 is a network access server that functions to provide connectivity between RAN 16 and packet-switched network 20. More particularly, PDSN 18 may function to translate between largely circuit-switched communications through RAN 16 and largely packet-switched communications over network 20. Alternatively or additionally, PDSN 18 may function principally as a router, to manage flow of packet-data between RAN 16 and network 20.

Preferably, packet-switched network 20 comprises one or more networks operating in accordance with the Internet Protocol (IP) and associated transport protocols. For instance, network 20 may include a wireless carrier's private packet-data enterprise network and/or the public Internet, as well as one or more other networks, through which packet data flows in accordance with the IP and TCP or UDP protocols. As such, each node sitting on network 20 preferably has a statically or dynamically assigned IP address to and from which the node engages in IP communications with other nodes on the network.

MMSC 22 is a server that functions to store and forward MMS messages to WCD 12 that are subscribers to the wireless service provider. In particular, MMSC 22 may receive an MMS message in the form of a prompt message from a message sender (network node 30). The prompt message will contain message content (prompt for media+schedule for media or prompt+link for return of media) and header information such as a designation of the intended recipient, WCD 12. After validating the message sender, MMSC 22 may then store the message content and make it available at a dynamically generated URL. MMSC 22 may then generate an MMS notification message and send the notification message over link 38 as an SMS message to WCD 12, which MSC 36 would forward via BSC 34, BTS 32, and air interface 14 to WCD 12.

Profile store 26 comprises data storage that maintains subscriber profile records for wireless subscribers, i.e., for users and/or devices. For instance, profile store 26 may contain a service profile record for each WCD served by RAN 16, such as for WCD 12 for instance. Each service profile record may specify services to which the WCD subscribes, such as services that the WCD is authorized to use according to a subscription plan or other plan.

For example, a service profile record for WCD 12 may indicate whether WCD 12 subscribes to a data communication service, such that WCD 12 is entitled to engage in an unlimited or specified quantity of wireless packet-data communication on a monthly or other recurring basis. As another example, the service profile record may indicate whether WCD 12 subscribes to a messaging communication service, such that WCD 12 is entitled to send and/or receive an unlimited or specified quantity of messages (e.g., MMS messages) on a monthly or other recurring basis. The service profile record can specify other types of service authorizations instead or in addition to these.

Profile store 26 may sit as a discrete element on network 20 as shown in FIG. 1. For instance, the profile store may take the form of a database server sitting as a node on network 20. Alternatively, the profile store may reside within, or be coupled with, one or more other elements, such as gateway 24 and/or MMSC 22 for instance.

In practice, profile store 26 can be used as a basis to authorize certain types of communications to and from a WCD. For instance, when packet-data is flowing through gateway 24 to or from WCD 12, gateway 24 may programmatically reference profile store 26 to determine whether the WCD 12 is authorized to engage in the data communication, and gateway 24 may allow or block the communication accordingly.

Further, in accordance with the exemplary embodiment, profile store 26 may serve as the basis to determine one or more service authorizations when an MMS message is being sent to a WCD, and as a basis to tailor the MMS notification accordingly. For instance, when an MMS message is being sent to WCD 12, MMSC 22 may reference the service profile of WCD 12 and thereby determine whether WCD 12 subscribes to data communication service and messaging service (e.g., MMS service). MMSC 22 may then accordingly insert one or more corresponding flags into the MMS notification, which WCD 12 will use as a basis to determine whether to perform a background download of the MMS content or a foreground download of the MMS content.

Mobile-IP home agent 28 functions in a manner well known in the art to assign a mobile-IP address to a WCD acquiring packet-data connectivity through RAN 16. For instance, after WCD 12 sends a packet-data origination request into RAN 16 and acquires a radio link (an air interface traffic channel assigned by BSC 34) and a data link (e.g., a point to point protocol (PPP) session with PDSN 18), WCD 12 may send a mobile-IP registration request, which PDSN (as mobile-IP foreign agent) would forward to home agent 28. Home agent 28 would then assign an IP address for use by WCD 12.

Message sender 30 is an entity that sends, in this context, a prompt message (content may vary) destined for receipt by WCD 12. As such, message sender 30 may be a client device, such as a personal computer or another WCD, or message sender 30 may be a server, such as network server of a government entity, business or other enterprise. In one arrangement, message sender 30 may include MMS application logic for generating and sending to MMSC 22 an MMS message that includes an MMS header and MMS content. Alternatively, message sender 30 may send its prompt message in some other form, such as by e-mail (e.g., SMTP), and a translation gateway (not shown) may translate the message into an MMS message for transmission in turn to WCD 12. Although message sender 30 is shown as a node on packet-switched network, message sender 30 may alternatively be another WCD or other MMS client device that sends its message to MMSC 22 in some other manner, such as through MSC 36 for instance.

Figure 2:
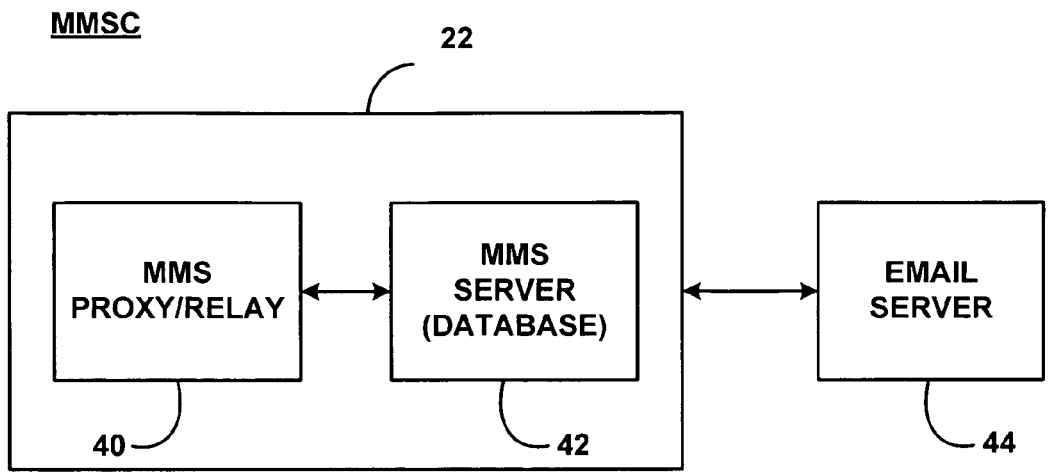
FIG. 2 is a more detailed diagram of the MMSC 22 of FIG. 1.

FIG. 2 is a more detailed illustration of the MMSC 22 of FIG. 1. The MMSC 22 includes a proxy/relay 40 providing an interface to the packet switched network 22 and over which MMS messages are sent to the wireless devices 12. The MMS server 42 provides storage services for multimedia messaging messages. This function could be combined with the proxy/relay 40. The functions of these entities are conventional and known in the art, see for example the WAP Forum MMS Architecture Overview, version 25, April 2001.

The MMSC may interface to an email server 44. The email server 44 could be used to receive prompt messages from the network node 30 of FIG. 3 and include transcoding logic to transcode email prompt messages to capture media to MMS format for storage in the MMS server 42.

Figure 3A:
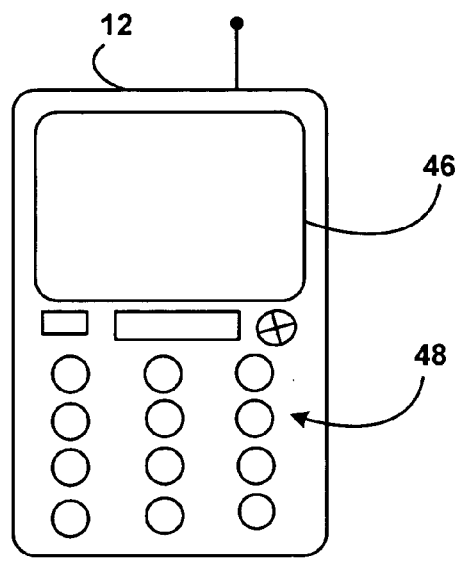
FIG. 3A is a front view of a wireless communications device.
Figure 3B:
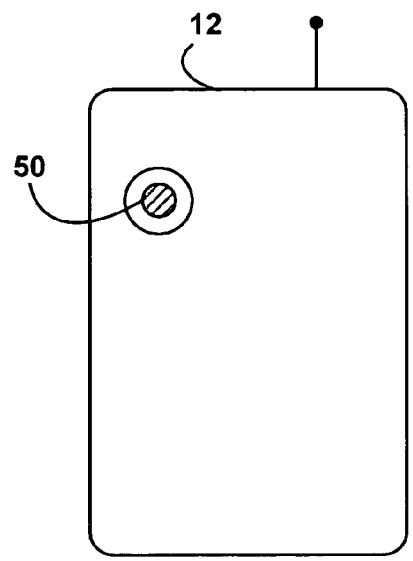
FIG. 3B is a rear view of a wireless communications device, showing a camera incorporated into the rear of the device.

FIGS. 3A and 3B are front and rear views, respectively, of a wireless communications device 12. The device includes a graphical user interface screen 46 for display of prompt messages and a set of manual user interface features such as buttons 48. The device 12 will preferably include a digital camera 50, shown in the rear of the device 12. The location of the camera can of course change. The device 12 may also include a microphone (not shown) for capturing acoustic signals, analog to digital conversion circuits and processing logic for conversion of digital acoustic signals into standardized format such as .wav or .mp3 format. The device 12 also includes a memory device (not shown, e.g., EEPROM or RAM) for storing captured media files.

B. Method of Operation

MMS messages are generated for receipt by wireless devices, e.g., by the message sender network node 30. The messages include a prompt for display on the wireless device prompting the use to capture media, a scheduling feature indicating when the prompt message is to be displayed, and a network address of where the media is to be sent to.

MMS messages generated by the sender 30 are sent to the MMSC 22 and stored in the MMS server 42 (FIG. 2). MMS proxy/relay 40 sends the message via the RAN 16 (FIG. 1) to the wireless device 12.

The wireless device decodes the MMS message and stores the message locally in memory. At a time dictated by the scheduling feature, the prompt is displayed on the wireless device. The prompt may include a link or URL address that the user may use to sent the media back to the requesting node. The destination need not be the same address as that of the sending node 30.

The user of the device captures the media and sends it back to the address specified in the prompt message. When the user captures the media (e.g., takes a picture of their meal or medications), the logic causing the presentation of the prompt message may also include instructions which detects the capturing of the image and then presents a prompt asking the user to confirm the media file just captured is the intended one (or is one in which the user is satisfied). For example, the sequence could work as follows:

1. Display prompt
2. Detect capturing of media
3. Display media and prompt user to confirm media is responsive to prompt
4. If Yes, proceed to send media to destination address automatically
5. If No, go back to step 2.

The sending of the media back to the network could be automated. For example, in the above process after the prompt is displayed, the user captures the media. The logic in the application could assume that the next media captured by the device 12 after the prompt message is displayed is in response to the prompt. The logic presents the prompt to the user and ask the user to confirm that the media is responsive to the prompt. If so, the media is automatically sent to the transmission buffer in the device 12 and sent over the RAN to the destination address. Alternatively, the media file could be sent at a later time, e.g., at a time established by user preferences, by a time established by a second scheduling feature in the prompt message, or otherwise.

C. Examples

Figure 4:
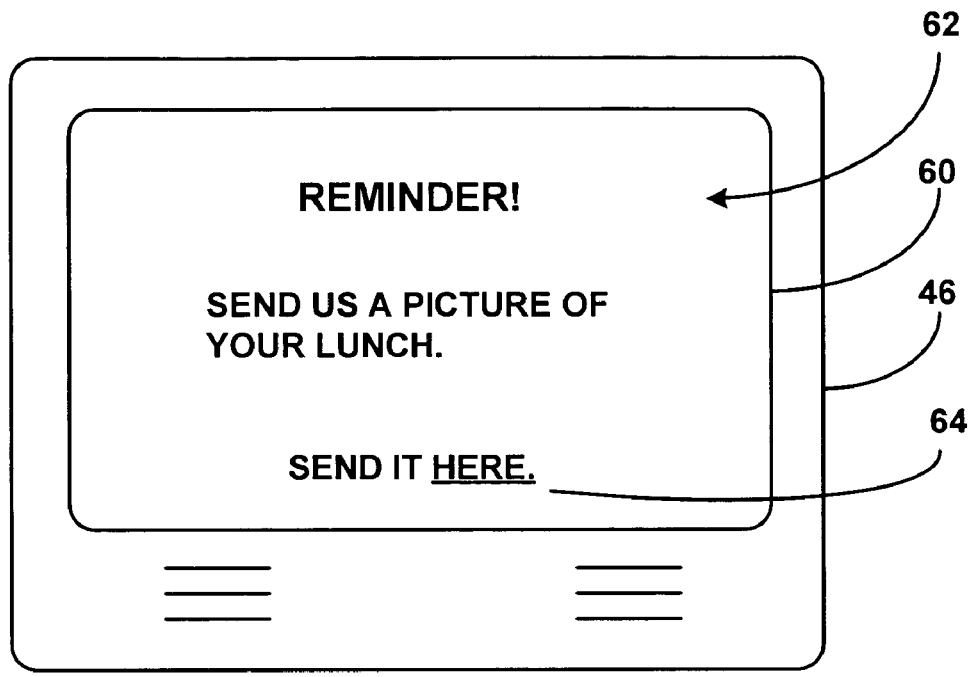
FIG. 4 is an illustration of a prompt message sent to the wireless device of FIG. 3A, showing a prompt to capture media and a network address (link) to send the media.

FIG. 4 is a sample prompt message 60 that is generated by the node 30, and sent via the MMSC 22 to the wireless device and displayed on the display 46 of the device 12. The message is in the form of a pop-up window 60 that pops up on the display 46 and includes include text 62 reminding the user to capture the media ("REMINDER! Please send us a picture of your lunch."). The timing of the pop-up window 60 is dictated by a scheduling feature contained in the prompt message sent to the device 12. The message further may include a link 64 where the user is to send the media. For example, the user minimizes the window 60, takes a picture of their lunch, toggles back to the window 60, and clicks on the link HERE 64. When the user clicks on the link HERE 64, an email message window pops up with the destination email address where the picture is to be sent to, and the user attaches the picture to the email message and clicks on "send."

Figure 5:
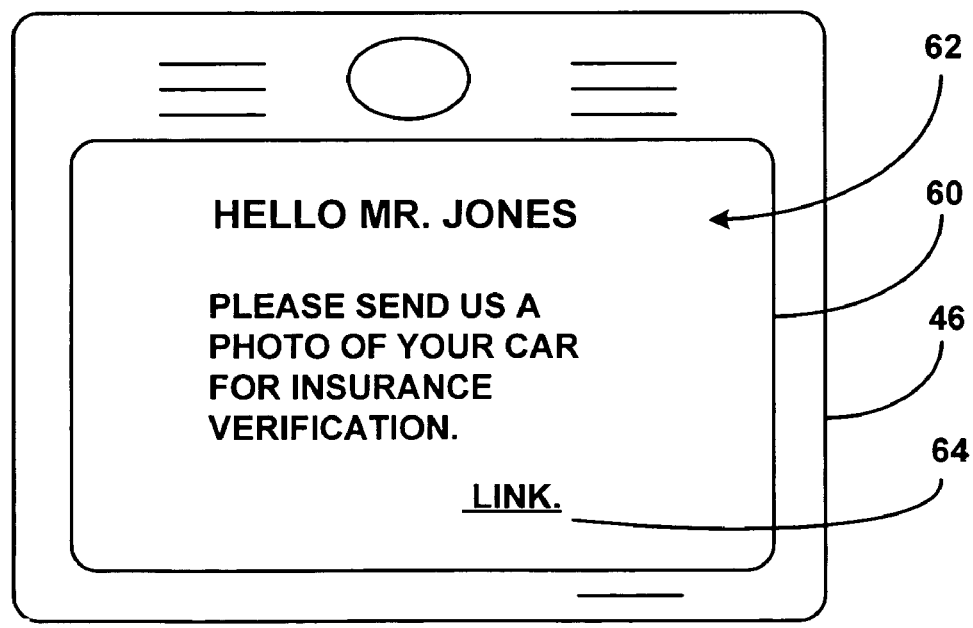
FIG. 5 is another example of a prompt message send to and displayed on the wireless device of FIGS. 1 and 3.

FIG. 5 is another example. The window 60 pops up on the display 46. This window contains text message 62. In this example, the user has purchased a new car and his insurance company is prompting him to take a photo of the new car for insurance verification. The user takes a photo of the car and sends them to the network address specified in the link 64.

Figure 6:
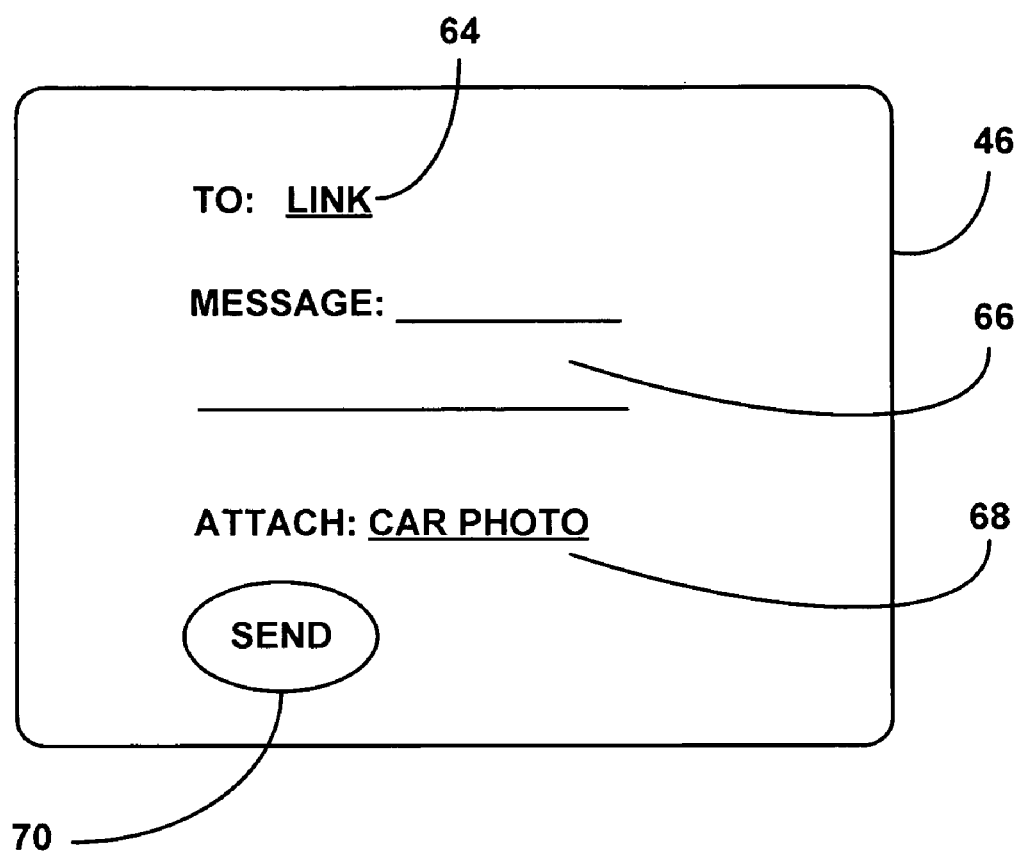
FIG. 6 is an illustration of a display on the device assisting the user to transmit the media to the network node.

FIG. 6 is an example of how the return of the media file may be performed. The display 46 shows a message including the link 64 address, a message field 66 where the user can add any text comments to the media file, and then an attachment field 68 where the user attaches the media file "car photo". The user clicks on the send icon 70 and the car photo and text in field 66 is sent to the link address 64.

Again, as noted above, in an alternative embodiment the sending process could also be automated wherein the device 12 includes logic that automates the sending of the media file back to the link address without the user interface steps indicated in the description of FIG. 6.

D. Messaging System

The invention can be implemented as a system including a message service node MMSC 22 which provides messaging services for a plurality of wireless communications devices 12. In this situation, the message service node 22 is preferably managed by a provider of wireless communications services and provides messaging services for a number of subscribers to the provider service.

The prompt message can be generated by a network node different from the message service node (e.g., message generator and sender 30) and transmitted to the message service node MMSC 22 for transmission to the wireless communications devices 12. For example, the network node 30 generating the messages could be a network node managed by a unrelated entity such as an insurance company, health or medical company, government agency, entertainment company, repair shop, or other type of entity. The message service node 22 provides a clearinghouse which collects all these messages, formats them if necessary in accordance with the required format for the message (e.g., in MMS form) and then sends them to the wireless devices on behalf of the entities that generated the prompt messages.

The process described above is thus implemented continually for a plurality of subscribers, with MMSC 22 receiving messages from potentially a wide variety of unaffiliated messages generators. The messages could arrive at MMSC 22 as MMS messages or they could be sent as email messages, stored in the email server 44 of FIG. 2 and transcoded into MMS format. The MMSC 22 may levy a small charge on either the subscribers or on the message generators on the use of the messaging services as described herein, depending on the revenue model for the system. The MMSC may make use of other elements of the wireless service provider enterprise network, such as AAA servers or accounting servers, in order to carry out this cost accounting task, the details of which are within the ability of persons skilled in the art.

E. Improved Wireless Devices

In still another aspect of this invention, a wireless communications device is provided that facilitates media "pull" from a network node 30. The device comprises transmit and receive circuitry (conventional) for communications with the network node over a radio access network; a graphical user interface presenting prompts and information to the user of the device; and a processor executing software instructions loaded in memory on the device. The software instructions include instructions for the processor to process an encoded message from a message service node and responsively display a prompt on the graphical user interface associated with the message. See e.g., FIGS. 4, 5 and 6. The prompt prompts the user of the device to transmit a media file to the network node. The prompt message includes a network address which may take the form of email address, IP address, etc., and indicates where the media file is to be transmitted. This address may be displayed in the form of a hyperlink, or as a destination address in a email message. As another example, the address may remain hidden from the user and consist of a IP address that is inserted into one or more TCP/IP packets as a destination address for the packet, with the packet(s) containing as payload a media file.

As noted earlier, the return network address may or may not be the same as the address of the sending node 30. For example, the wireless service provider could provide a data warehouse for storing response media files and the network entities that request pull of the media could access the media files from the data warehouse. As another example, one network node creates prompt messages and sends them to the MMSC 22, but another node (e.g., a database server) receives all response messages.

While presently preferred and alternative embodiments have been described, variation from the illustrated embodiments is possible without departure from the scope of the invention. The scope is to be determined by reference to the appended claims.

The invention claimed is:

1. A method of obtaining media from a wireless communications device, comprising the steps of:
    a) sending an encoded message from a first node to the wireless communications device, the encoded message comprising a prompt displayable at the wireless communications device prompting or reminding a user of the wireless communications device to capture media;
    b) including in the encoded message a schedule feature indicating to display the prompt at periodic time intervals;
    c) including in the encoded message a network address where the captured media is to be sent by the wireless communications device, wherein the network address is associated with a second node; and
    d) including in the encoded message instructions to present a second prompt asking the user of the wireless communications device to confirm that the captured media is responsive to the prompt.

2. The method of claim 1, wherein the media comprises an image and wherein the encoded message prompts the wireless communications device to capture the image with a camera incorporated in the wireless communications device.

3. The method of claim 1, wherein the encoded message comprises a Multimedia Messaging Service (MMS) message.

4. The method of claim 1, wherein the first node further comprises a memory for storing the encoded message and wherein the encoded message is sent periodically to the wireless communications device.

5. The method of claim 1, wherein the first node provides messaging services for a plurality of wireless communications devices and wherein the encoded message is generated by the second node and transmitted to the first node for transmission to the wireless communications device.

6. The method of claim 5, wherein the first node is managed by a provider of wireless communications services for the wireless communications device, and wherein the second node generating the encoded message is managed by an entity independent of the provider of wireless communications services, whereby the node provides messaging services prompting media capture for a plurality of wireless communications devices for entities independent of the provider of wireless communications services.

7. A wireless communications device facilitating media pull from a network node, comprising:

transmit and receive circuitry for communications with the network node over a radio access network;

a graphical user interface presenting prompts and information to a user of the wireless communications device; and a processor executing software instructions loaded in memory on the wireless communications device, wherein the software instructions comprise instructions for the processor to process an encoded message from a message service node and to responsively display a prompt on the graphical user interface associated with the encoded message, wherein the prompt prompts the user of the wireless communications device to transmit a media file to the network node;

and wherein the encoded message includes a scheduling feature indicating to display the prompt at periodic time intervals and a network address where the media file is to be transmitted, wherein the network address is associated with the network node, and wherein the software instructions further include instructions for the processor to detect capture of the media file, to display the media file, and to display a second prompt to the user of the wireless communications device to confirm that the media file is responsive to the prompt of the encoded message, wherein in response to a received confirmation that the media file is responsive to the prompt of the encoded message, the processor responsively transmits the captured media file to the network node.

8. The device of claim 7, wherein the wireless communications device includes an apparatus for capturing the media file.

9. The device of claim 8, wherein the apparatus comprises a digital camera.

10. The device of claim 7, wherein the wireless communications device comprises a cellular telephone incorporating a digital camera.

11. The device of claim 7, wherein the encoded message comprises a Multimedia Messaging Service (MMS) message.

12. The device of claim 7, wherein the media file comprises an image file.

13. A system for pulling media from wireless communications devices, comprising:

a) a node on a packet switched network generating an encoded message for wireless communications devices, the encoded message comprising a 1) prompt for a wireless communications device to capture media, wherein the node on the packet switched network designates the wireless communications device as a recipient of the prompt, 2) a network address to send the media, wherein the network address is associated with the node on the packet switched network, 3) a scheduling feature that indicates to display the prompt at periodic time intervals on a screen of the wireless communications device, and 4) instructions to present a second prompt asking the user to confirm that the captured media is responsive to the prompt;

b) a messaging service node coupled to the packet switched network receiving the encoded message generated by the node; the messaging service node transmitting the encoded message to the wireless communications devices;

c) wherein the messaging service node is managed by a provider of wireless communications services and wherein the node is managed by an entity or entities independent of the provider of wireless communications services.

14. The system of claim 13, wherein the encoded message are sent as Multimedia Messaging Service (MMS) messages to the messaging service node.

15. The system of claim 13, wherein the encoded message prompt the wireless communications devices to capture an image.

16. The system of claim 15, wherein the encoded message are sent to the messaging service node in accordance with a schedule maintained by the node.

17. The system of claim 13, wherein the encoded message comprise Multimedia Messaging Service (MMS) messages and wherein the messaging service node comprises a node providing MMS messaging services for a plurality of wireless communications devices subscribing to services of the provider of wireless communications services.

18. The system of claim 13, wherein the node comprises a server managed by an entity selected from the group of entities consisting of a) an insurance company, b) a company providing health or medical services, c) a government entity and d) an entertainment company.

19. The system of claim 13, wherein the media comprises audio.

20. The method of claim 1, wherein the network address is a URL address.

* * * * *